(12) United States Patent
Steimel et al.

(10) Patent No.: US 7,077,976 B2
(45) Date of Patent: Jul. 18, 2006

(54) PHOSPHONAMIDE AND PHOSPHONAMIDE BLEND COMPOSITIONS TO TREAT WATER

(75) Inventors: Lyle Steimel, Forest Park, OH (US); James Emerson, Cincinnati, OH (US); Sue Ann Balow, Maineville, OH (US)

(73) Assignee: JohnsonDiversey, Inc., Sturtevant, WI (US)

( * ) Notice: Subject to any disclaimer, the term of this patent is extended or adjusted under 35 U.S.C. 154(b) by 0 days.

(21) Appl. No.: 11/258,301

(22) Filed: Oct. 25, 2005

(65) Prior Publication Data

US 2006/0131241 A1    Jun. 22, 2006

Related U.S. Application Data

(62) Division of application No. 11/015,781, filed on Dec. 17, 2004, now abandoned.

(51) Int. Cl.
*C02F 5/14* (2006.01)
(52) U.S. Cl. ............... 252/180; 210/700; 544/157; 564/12
(58) Field of Classification Search ............... 210/700
See application file for complete search history.

(56) References Cited

U.S. PATENT DOCUMENTS

| | | | |
|---|---|---|---|
| 2,676,962 A * | 4/1954 | Lewis et al. ............... 544/84 |
| 3,210,350 A | 10/1965 | D'Alelio .................. 260/248 |
| 3,699,118 A | 10/1972 | Donham ................. 260/309.6 |
| 3,853,471 A * | 12/1974 | Rittersdorf et al. ......... 436/66 |
| 3,939,226 A | 2/1976 | Scharf ...................... 260/932 |
| 3,954,761 A | 5/1976 | Redmore ................ 269/268 K |
| 4,006,182 A | 2/1977 | Plöger et al. ............ 260/502.5 |
| 4,066,398 A | 1/1978 | Hwa |
| 4,678,840 A | 7/1987 | Fong et al. ................. 525/340 |
| 4,722,805 A | 2/1988 | Martin .................. 252/389.21 |
| 4,874,541 A | 10/1989 | Steimel et al. |
| 4,891,141 A | 1/1990 | Christensen et al. |
| 5,143,622 A | 9/1992 | Fong et al. ................. 210/700 |
| 5,213,691 A | 5/1993 | Emmons et al. ............ 210/700 |
| 5,380,466 A | 1/1995 | Martin .................. 252/389.22 |
| 5,424,032 A | 6/1995 | Christensen et al. |
| 5,800,732 A | 9/1998 | Coughlin et al. |
| 5,961,845 A | 10/1999 | List et al. |
| 6,083,403 A | 7/2000 | Tang et al. ................. 210/700 |
| 6,797,197 B1 * | 9/2004 | Steimel et al. ......... 252/188.28 |

FOREIGN PATENT DOCUMENTS

WO    WO 03/008426 A1    1/2003

* cited by examiner

*Primary Examiner*—Peter A. Hruskoci
(74) *Attorney, Agent, or Firm*—Wood, Herron & Evans, L.L.P.

(57) ABSTRACT

The invention is a water treatment composition comprising at least one phosphonamide and blends thereof and a method to treat water. As phosphonamides are generally odorless, and typically solids, phosphonamide and phosphonamide blend compositions are generally odorless, conveniently processed and manufactured, and safely used without risks of exposure to odors and vapors associated with the corresponding amines. Advantageously, phosphonamides blended with amino-phosphate esters provide useful treatment compositions. The inventive compositions are generally used to treat water contained in water flow systems such as boilers and cooling towers.

21 Claims, No Drawings

PHOSPHONAMIDE AND PHOSPHONAMIDE BLEND COMPOSITIONS TO TREAT WATER

RELATED APPLICATIONS

This application is a divisional application of application Ser. No. 11/015,781, entitled Phosphonamide and Phosphonamide Blend Compositions and Method to Treat Water, filed Dec. 17, 2004 (abandoned); which is related to application Ser. No. 10/231,531, also entitled Phosphonamide and Phosphonamide Blend Compositions and Method to Treat Water, filed Aug. 30, 2002 (abandoned), and application Ser. No. 10/348,161, also entitled Phosphonamide and Phosphonamide blend Compositions and Method to Treat Water, filed Jan. 21, 2003 (which issued as U.S. Pat. No. 6,846,419 on Jan. 25, 2005)

FIELD OF THE INVENTION

The present invention relates to a composition and method to treat water. More particularly, the invention provides a composition comprising at least one phosphonamide or phosphonamide blends to treat water.

BACKGROUND OF THE INVENTION

Water for heating and cooling apparatus must be purified or treated to avoid a plurality of problems. More specifically, boilers and cooling towers require pure water for optimal performance. However, the water coming into these systems is generally impure and contains contaminants which can foul the boiler and cooling tower.

Feed water is generally contaminated with gases, such as oxygen and carbon dioxide. In addition, water can leach impurities from the air. These impurities lead to scale formation, corrosion, and pitting. A major contaminant in many water systems is iron, often leached from water lines.

In cooling towers, such problems may escalate due to evaporation of the water, thereby increasing concentration of the contaminants and resulting in a higher rate of subsequent corrosion and deposition tendencies. Higher temperatures also tends to increase corrosion potential. A longer retention time of contaminants in the water coupled with warmer water tends to reduce the effectiveness of heat transfer surfaces and increases the potential for microbiological growth.

Currently there are a variety of different physical and chemical treatments for contaminated water. Conventional treatments for water systems, such as a boiler, have included the use of amines, particularly to scavenge oxygen and neutralize carbon dioxide. These amines are generally volatile having boiling points comparable to the elevated temperatures achieved in the boiler and generally vaporize into the steam to treat the resulting condensate. However, amines, commonly used to treat water, are typically commercially available only as liquids. Conventional water treatment compositions containing such amines are generally prepared and stored as liquids. These liquid compositions typically emit repugnant and potentially toxic odors which may be detected during manufacture, packaging, or shipping processes, and particularly during the use in treating boiler water.

Corrosion inhibiting chemicals as disclosed in U.S. Pat. No. 4,066,398 have been used to treat contaminated water. U.S. Pat. No. 3,510,436 discloses the use of organic phosphates or phosphonates in combination with zinc and/or mercaptobenzothiazole for corrosion inhibition in water systems including cooling towers. Compositions utilizing chromates and inorganic polyphosphates have been used to inhibit corrosion of metal surfaces in contact with cooling tower water. However, such treatments are undesirable, both from the viewpoint of handling personnel health and also problems associated with waste disposal. Phosphates are generally non-toxic. However, due to hydrolysis of polyphosphates to orthophosphates and the limited solubility of calcium orthophosphate, which is likely to form, it has been impossible in many instances to maintain adequate concentrations of phosphates. Furthermore, from a water pollution standpoint, effluent containing a sufficiently high phosphate residual, may serve as a nutrient to aquatic life. For these reasons, the use of chromates, inorganic phosphates and other phosphates have been entirely unsatisfactory.

Thus, there remains a need to provide a composition to treat water in water flow systems effectively and safely, from a health and handling perspective, with minimal waste disposal problems.

SUMMARY OF THE INVENTION

Accordingly, the invention is directed to a composition comprising at least one phosphonamide or blends thereof which may be added in amounts effective to treat water in water flow systems. Forming a phosphonamide from an amine generally eliminates odors and vapors emitted by the corresponding amine. Accordingly, phosphonamides reduce exposure related health and safety risks to the user or handling personnel associated with the preparation, manufacture, packaging, and general application of amines that have been used to treat water. In addition, the generally solid nature of a phosphonamide, or blend of phosphonamides, typically allows the treatment composition to be formulated into a convenient dry solid or powder.

The phosphonamide is an amine derivatized to an amide by reacting the amine with a phosphonic acid. The phosphonamide may be fully or partially formed depending on the mole ratios and/or weight ratios of the particular amine and phosphonic acid. Typically, amine to phosphonic acid weight ratios of about 1:1 to about 10:1 are suitable.

Suitable amines used to form the phosphonamide include, for example, cyclohexylamine, morpholine, octadecylamine, N,N-dimethyl-1,3-propandiamine, and ammonium hydroxide. Suitable phosphonic acids include, for example, aminotri(methylene phosphonic acid), 1-hydroxyethylidene-1,1-diphosphonic acid, and 2-phosphono-butane-1,2,4-tricarboxylic acid.

Alternatively, the treatment composition may comprise a blend of phosphonamides formed by blending together individual phosphonamides or by reacting a blend of two or more amines simultaneously with a phosphonic acid. Advantageously, non-solid phosphonamides may be blended with solid phosphonamides to form a solid composition. In addition, blending phosphonamides provide the advantage of improving water solubility of the final composition thereby providing effective and economical water treatment.

The treatment composition may also include other components necessary to treat contaminants in the water by mixing these components with the phosphonamide. For example, an amino-phosphate ester generally formed from a hydroxy amine and a phosphonic acid may be blended with a phosphonamide. Additives such as a hardness control agent may also be included in the final composition.

The precise quantities of the phosphonamide and phosphonamide blends in the final treatment composition added to the water may vary as desired by the user. Concentrations will generally depend upon the desired formulation of composition, concentration of components in the water, and the type and degree of impurities and contaminants in the water.

The present invention will be further appreciated in light of the following detailed description.

DETAILED DESCRIPTION OF THE INVENTION

The invention is directed to a composition and method of treating contaminants and impurities in water. More specifically, the composition comprises at least one phosphonamide formed from an amine and a phosphonic acid. Added benefits come from blending different phosphonamides, as well as other components, into the final treatment composition. Generally, phosphonamides are odorless and solid in nature, thereby allowing the inventive composition to be a safe and convenient treatment product. The odorless nature of the phosphonamide eliminates health and safety risks associated with amine odors which are often detected during handling, processing, and manufacture of the product.

The phosphonamide is generally formed by reacting an amine with a phosphonic acid to affect a corresponding covalent amide bond. The amine used to form the corresponding phosphonamide may be any primary or secondary amine. For example, without limitation, the amine may have a general formula $HN-R^1R^2$, where $R^1$ and $R^2$ are independently selected from the group consisting of H, alkyl, cycloalkyl, aryl, and heteroaryl organic structures having up to 10 atoms selected from the group consisting of C, N, and O. The term "alkyl" as used herein, generally refers to a straight or branched hydrocarbon chain of varying length or number of atoms, such as from 1–10 atoms. The term "cycloalkyl", as used herein, refers to an unsaturated cyclic ring comprising carbon, nitrogen, or oxygen atoms in the ring. The term "aryl", as used herein, refers to an aromatic ring consisting of carbon atoms, and the term "heteroaryl", as used herein, refers to an aromatic ring having heteroatoms including nitrogen and oxygen. Alternatively, $R^1$ and $R^2$ taken together with a nitrogen to which they are attached, may form a 5- or 6-membered ring containing 0–2 additional heteroatoms selected from nitrogen or oxygen. For example, morpholine, a cyclic amine wherein $R^1$ and $R^2$ taken together forms a 6-member ring containing an oxygen atom at the 4-position, may be used to form a phosphonamide for the treatment composition. In addition, the $R^1$ and $R^2$ substitutions may bear other functional groups, such as ethers or amines, which do not participate in the amide bond formation.

Examples of suitable amines include, but are not limited to, cyclohexylamine, octadecylamine, and N,N-dimethyl-1,3-propanediamine, and even ammonium hydroxide. The amines may be purchased commercially from vendors such as Aldrich Chemical Co., or synthesized as desired, to optimize physical and chemical properties of the resulting phosphonamide.

A variety of phosphonic acids and derivatives thereof may be used to react with the amine. Persons of ordinary skill in the art readily understand that the term "phosphonic acid", as used herein, generally refers to phosphonic acids having different general formulae which may react with an amine to produce a phosphonamide. For example, a phosphonic acid having the general formula $(OR)_2-P(O)OH$ wherein the R groups may be identical or different, is suitable for the invention. Alternatively, a phosphonic acid having a general formula $(OH)_2-P(O)OR$ is also suitable. Thus, a phosphonamide formed from an amine and a phosphonic acid of the former formula will have a general structure: $(OR)_2-P(O)N-R^1R^2$, whereas, a phosphonamide formed from an amine and a phosphonic acid of the latter formula may have a general structure: $RO-P(O)-(N-R^1R^2)_2$. Suitable phosphonic acids for use in the invention may be commercially purchased or synthesized depending upon desired properties of the final treatment composition. Examples of suitable phosphonic acids include, but are not limited to, amino tri(methylene phosphonic acid), 1-hydroxyethylidene-1-1-diphosphonic acid, and 2-phosphono-butane-1,2,4-tricarboxylic acid.

The phosphonamide may be purchased commercially, if available, or synthesized using conventional synthetic methods and reagents necessary to form the amide bond. For instance, the phosphonamide may be formed by mixing the amine and phosphonic acid together using conventional mixing apparatus and methods. For example, the amine, in desired molar or weight quantities, may be first added to a powder blender. The blender may then be activated while a phosphonic acid, in desired molar or weight quantities, is added to the amine. Depending on the class and structure of the amine and particular phosphonic acid, reaction of the amine with the phosphonic acid may be sufficiently exothermic to form the amide bond. Alternatively, heat or catalysts may be utilized to optimize the reaction and provide maximum conversion of the amine and phosphonic acid to the corresponding phosphonamide. With most phosphonamides, as the amide bond forms, the reaction mixture precipitates to generate a solid phosphonamide product. The resulting phosphonamide is then cooled and processed by conventional techniques to eliminate by-products and catalysts, if any, and to purify the phosphonamide. Particularly useful phosphonamides include, without limitation, phosphonamides formed from amines reacted with 1-hydroxyethylidene-1-1-diphosphonic acid, and 2-phosphono-butane-1,2,4-tricarboxylic acid respectively.

It is desirable and economical, for optimal water treatment and solid formulation, to use a composition comprising a blend of more than one phosphonamide. The term 'blend' as used herein, is intended to mean a mixture or combination of more than one component, such as a phosphonamide. Phosphonamide blends facilitate formation for a solid treatment composition while optimizing the level and specificity of treatment by utilizing different amines. In addition, phosphonamide blends have the advantage of minimizing or eliminating hygroscopicity or deliquescence of a treatment composition where one phosphonamide is mildly hygroscopic in nature, i.e., tending to absorb moisture over time, thereby posing a risk to the stability of the phosphonamide and the overall treatment composition. For example, blending a non-hygroscopic phosphonamide with a mildly hydroscopic phosphonamide may provide a phosphonamide blend composition which is stable, resistant to absorption of moisture, and has a long shelf life. In one embodiment of the invention, the treatment composition comprises a blend of at least two phosphonamides formed from different amines reacted with a phosphonic acid.

In addition, blending phosphonamides may provide the advantage of improving the water solubility of a final treatment composition which may include a non-water soluble phosphonamide. One factor influencing the water solubility of a phosphonamide is the hygroscopicity or deliquescent nature of the phosphonamide discussed above. Water solubility may be improved by blending desirable hygroscopic or deliquescent components, such as desired phosphonamides, in quantities resulting in a composition having greater solubility characteristics. For example, blending a non-hygroscopic phosphonamide with a liquid or semi-solid component, such as an amino-phosphate ester, discussed in more detail further below, may improve water solubility of the final composition.

Blends of phosphonamides may be prepared by combining more than one phosphonamide, each prepared individually, and blending them together. Alternatively, blends of phosphonamides may be prepared by mixing different amines, i.e., amines having different R groups, together in a blender, adding a single phosphonic acid to the mixture of amines, and causing the mixture to react to form a mixture or blend of different phosphonamides. For example, a mixture of two or more amines in desired molar quantities or weight percent may be blended with a desired phosphonic acid.

The molar or weight ratios of the amines to phosphonic acid should be in the range of about 1:1 to about 10:1. An amine to phosphonic acid mole ratio of equal to or greater than 1:1 will generally allow complete conversion of every amine to a corresponding phosphonamide. In one embodiment of the invention, the blend has an amine to phosphonic acid mole ratio ranging from about 3:2 to about 4:1 to provide adequate water treatment. Persons of ordinary skill in the art readily understand that some phosphonic acids, depending upon the general formula discussed above, may utilize two molecules of amine per molecule of phosphonic acid to form a phosphonamide. For instance, a phosphonic acids having the general formula $(OH)_2$—P(O)OR may react with two molecules of an amine to form a phosphonamide having two moles of the amine per mole of phosphonic acid. In this case, the corresponding phosphonamide may be completely formed where the amine to phosphonic acid mole ratio is at least 2:1.

The amount of the phosphonamide, or blends thereof, used to effectively treat water will depend upon the user and other factors such as the level of the impurities and contaminants in the water, the desired water concentration of the phosphonamides, and the desired formulation of the final composition. Effective concentrations of the phosphonamide in the water may generally vary. For example, in a steam boiler, the concentration of the phosphonamide should be in the range of 1–200 ppm for effective treatment of water, and 1–200 ppm for effective treatment of condensate in the boiler feed lines.

To obtain such water concentrations, sufficient amounts of the phosphonamide composition must be added to the water. The precise amount will depend upon the particular phosphonamide concentration in the composition. The phosphonamide may generally be present in the composition in at least about 10% by weight of the final treatment composition. Water may be more effectively treated where the phosphonamide concentration is higher. Where the composition includes a blend of two or more phosphonamides, it is beneficial to have each individual phosphonamide present in at least about 10% by weight of the final composition. In one embodiment, the treatment composition includes morpholine-1-hydroxy-ethylidene-1-phosphoryl-phosphonamide, present in a range of about 10% to about 50% by weight, and cyclohexylamine-1-hydroxy-ethylidene-1-phosphoryl-phosphonamide, present in a range of about 10% to about 66% by total weight of the amine component in the final composition.

Further aspects of the invention include phosphonamides blended with other components to beneficially treat water. One such component is an amino-phosphate ester. Amino-phosphate esters are particularly useful in treating water at elevated temperatures, such as boiler water and condensate, as the amino-phosphate ester generally degrades at the elevated temperature, at atmospheric or slightly higher pressure to release the hydroxy amine and the phosphonic acid into the water. Amino-phosphate esters, depending on the amine, are generally liquids.

Amino-phosphate esters may generally be formed from a hydroxy amine and a phosphonic acid. The hydroxy amine may be any hydroxy amine commercially available from vendors, such as Aldrich Chemical Co., or synthesized. Hydroxy amines can be synthesized by modifying an amine core molecule to attach the requisite terminal hydroxy group. Conventional methods to incorporate the hydroxy terminus including conversion of a terminal functional group to a hydroxyl group may be used. Such methods are disclosed in Advanced Organic Chemistry, $4^{th}$ Ed., authored by Jerry March, published in 1992. Examples of suitable hydroxy amines for the amino phosphate ester include N,N-diethylethanolamine, 2-amino-2-methyl-1-propanol, 1,1-dimethylamine-propanol, and 2-dimethylamino-2-methyl-1-propanol.

Suitable phosphonic acids used to form the amino-phosphate esters include, without limitation, those suitable for forming the phosphonamides discussed above. Preparation of the hydroxylamine-phosphonic acid ester may be accomplished by synthetic methods as known to persons skilled in the art. For example, the preparation of amino phosphate esters is described in U.S. Pat. No. 3,477,956 and U.S. Pat. No. 3,528,502.

Blends of phosphonamides and amino-phosphate esters may be prepared by mixing a plurality of amines, including one or more hydroxy amines, with a phosphonic acid in desired molar ratios or weight percent to effectively form the corresponding phosphonamides and amino-phosphate esters. For example, in one embodiment of the invention, the composition includes a blend of morpholine-1-hydroxy-ethylidene-1-phosphoryl-phosphonamide, cyclohexylamine-1-hydroxy-ethylidene-2-phosphoryl-phosphonamide, and diethylaminoethanol-1-hydroxy-ethylidene-1-phosphoryl-phosphate ester wherein each phosphonamide is present in the composition in at least about 10% by weight, and the amino-phosphate ester is present in at least about 10% by weight of the amine. In preparing this blend, the cumulative amine to 1-hydroxy-ethylidene-1,1-diphosphonic acid mole ratio is generally in the range of about 1:1 to about 10:1.

Such phosphonamide-amino phosphate ester blends provide advantageous compositional properties and water treatment qualities. As discussed earlier, blending one or more phosphonamides with one or more amino-phosphate ester may provide the advantage of optimizing the possibility of a solid composition where one component is hygroscopic or essentially a liquid in nature. Depending upon the precise weight ratios of non-deliquescent components relative to the deliquescent components, the blended composition may be formulated into a convenient solid. For example, a blend of a mildly hygroscopic morpholine-HEDP amide and a liquid diethylaminoethanol-HEDP ester, with a non-hygroscopic cyclohexylamine-HEDP amide provides a composition which may be a solid where the weight ratio of cyclohexylamine-HEDP amide is about or greater than 25%.

Furthermore, such blend compositions advantageously improve water solubility of the final treatment composition, thereby improving the effectiveness of the water treatment. For instance, a blend of morpholine-HEDP amide, cyclohexylamine-HEDP amide, and diethylaminoethanol-HEDP ester in the right proportions may have a water solubility of 50 weight percent per volume of water or greater. For example, a blend formed from a mixture of morpholine in about 13–14% by weight, cyclohexylamine in about 32–33% by weight, and diethylaminoethanol in about 54% by weight, was reacted with 1-hydroxy-ethylidene-1,1-diphosphonic acid at different cumulative amine to 1-hydroxy-ethylidene-1,1-diphosphonic acid mole ratios ranging from about 3:2 to about 4:1 produced blend compositions having advantageous water solubilities in the range of from about 45% to about 80% soluble. In a case where a desirable blend composition has marginal water solubility, then a larger amount of the composition would have to be added to effectively treat the water.

Additional components which may be added to the inventive composition include, without limitation, additional oxygen scavenging agents, alkalinity control agents, hardness reducing agents, corrosion inhibiting agents, carbonic acid neutralizing agents, and iron controlling agents. These components may be formulated with the phosphonamides, along with amino-phosphate esters, to form an all-in-one treatment composition by the addition of concentrated forms of each component at relative concentrations to allow the formulated treatment composition to be dispensed into the water to attain the desired use concentrations. The actual amount of each component added to the concentrated formulation generally depends on, among other factors, the precise intended use concentrations and the concentration of each component as purchased. For example, in one embodiment, a sulfonated water soluble polymeric hardness control agent, such as Versiflex 1, commercially available from Alco, Inc. may be added in about 10% to about 50% by weight of the final composition to reduce hardness in the water.

The inventive water treatment compositions are also useful for treating water in cooling towers. The particular treatment composition will generally vary depending upon the quantity of water, the temperature of the water, and the level of contamination. For example, in one embodiment, a cooling tower treatment composition includes a phosphonamide formed from mixing a cyclohexylamine with 1-hydroxyethylidene-1,1-diphosphonic acid, and having an amine to phosphonic acid mole ratio of from about 2:1 to about 10:1. This phosphonamide has the advantage of being a solid. Generally, cooling tower water may be effectively treated if the phosphonamide is added in an amount to obtain a water concentration in the range of 1–20 ppm.

In one composition particularly suited for cooling tower water is the reaction product of cyclohexylamine and HEDP. The ratio of amine to HEDP should be in the range of from about 1 to 1 to about 10 to 1. Further, cyclohexylamine in about 33% by weight and 1-dihydroxyethylidene-1,1-diphosphonic acid in about 37% by weight, can be combined with a copolymer, which may be a liquid, in about 30% by weight, to form a solid. Such a blend has minimal or no hydroscopicity and has a prolonged shelf life while maintaining the solid form. Examples of polymers which may be combined with a phosphonamide to treat water in cooling towers include, without limitation, polyacrylate.

Accordingly, the invention is a composition and method of treating water by adding an amount of a phosphonamide or blends thereof to treat the water. The phosphonamide may be applied as a concentrated liquid, a dry powder, or as one of many components in a treatment composition formulated as a concentrated liquid or, more preferably, as a dry powdery solid. Phosphonamides do not produce pungent odors typically associated with amines. Furthermore, they provide a solid which can be added to boilers and cooling towers to provide an amine and a phosphate.

While the present invention has been illustrated by a description of various embodiments, and while these embodiments have been described in detail, it is not the intention of the applicants to restrict or in any way limit the scope of the appended claims to such detail. Additional advantages and modifications will readily appear to those skilled in the art. Therefore, the invention in its broader aspects is not limited to the specific details and representative methods as shown and described. Accordingly, it is apparent that certain modifications or alterations can be made without departing from the spirit or scope of the invention set forth in the appended claims.

What is claimed is:

1. A water treatment composition comprising at least one phosphonamide formed by reacting an amine selected from the group consisting of cyclohexylamine, morpholine, octadecylamine, N,N-dimethyl-1,3-propandiamine, and ammonium hydroxide, and
    a phosphonic acid selected from the group consisting of aminotri(methylene phosphonic acid), 1-hydroxyethylidene-1,1-diphosphonic acids and 2-phosphono-butane-1,2,4-tricarboxylic acid,
and blends thereof to treat water.

2. The composition of claim 1 wherein the blend comprising at least two phosphonamides formed from at least two amines and a phosphonic acid, said blend having a cumulative amine to phosphonic acid mole ratio in the range of from about 1:1 to about 10:1.

3. The composition of claim 2 wherein the phosphonamide is present in at least about 10% by weight of the composition.

4. The composition of claim 1 further comprising an amino-phosphate ester formed from a hydroxyamine and a phosphonic acid.

5. The composition of claim 4 wherein the amino-phosphate ester is present in at least about 10% by weight of the composition.

6. The composition of claim 4 wherein the hydroxyamine is selected from the group consisting of N,N-diethylethanolamine, 2-amino-2-methyl-1-propanol, 1,1-dimethylaminepropanol, and 2-dimethylamino-2-methyl-1-propanol.

7. The composition of claim 1 further comprising a hardness control agent.

8. The composition of claim 1 wherein the phosphonamide is present in at least about 10% by weight of the composition.

9. The composition of claim 1 wherein the composition is a solid.

10. A water treatment composition comprising at least one phosphonamide formed by reacting a compound selected from the group consisting of cyclohexylamine, morpholine, octadecylamine, N,N-dimethyl-1,3-propandiamine, and ammonium hydroxide, and mixtures thereof; and
    a phosphonic acid selected from the group consisting of aminotri(methylene phosphonic acid), 1-hydroxyethylidene-1,1-diphosphonic acid, and 2-phosphono-butane-1,2,4-tricarboxylic acid and mixtures thereof.

11. The composition of claim 10 further comprising an amino-phosphate ester formed from a hydroxyamine and a phosphonic acid.

12. The composition of claim 11 wherein the amino-phosphate ester is present in at least about 10% by weight of the composition.

13. The composition of claim 11 wherein the hydroxyamine is selected from the group consisting of N,N-diethylethanolamine, 2-amino-2-methyl-1-propanol, 1,1-dimethylamine-propanol, and 2-dimethylamino-2-methyl-1-propanol.

14. The composition of claim 10 further comprising a hardness control agent.

15. The composition of claim 14 wherein the composition is a solid.

16. The composition of claim 14 wherein the phosphonamide is present in at least about 10% by weight of the composition.

17. The composition of claim 14 wherein the hardness control agent is a sulfonated water soluble polymeric compound.

18. A water treatment composition comprising a blend of:
   at least two phosphonamides,
      said phosphonamides formed from a reaction of a first phosphonic acid and at least two amines independently selected from the group consisting of cyclohexylamine, morpholine, octadecylamine, N,N-dimethyl-1,3-propanediamine, and ammonium hydroxide; and
   an amino-phosphate ester;
      said phosphate ester formed from a reaction of a second phosphonic acid and a hydroxyamine selected from the group consisting of N,N-diethylethanolamine, 2-amino-2-methyl-1-propanol, 1,1-dimethylamine-propanol, and 2-dimethylamino-2-methyl-1-propanol.

19. The composition of claim 18 wherein the first phosphonic acid is the same as the second phosphonic acid.

20. The composition of claim 18 wherein the first and second phosphonic acids are independently selected from the group consisting of aminotri(methylene phosphonic acid), 1-hydroxyethylidene-1,1-diphosphonic acid, and 2-phosphono-butane-1,2,4-tricarboxylic acid.

21. A composition comprising a blend of:
   a morpholine-1-hydroxy-ethylidene-phosphoryl-phosphonamide present in at least about 10% by weight;
   a cyclohexylamine-1-hydroxy-ethylidene-phosphoryl-phosphonamide present in at least about 10% by weight; and
   a diethylaminoethanol-1-hydroxy-ethylidene-phosphoryl-phosphonate ester present in at least about 10% by weight of the blend.

* * * * *

UNITED STATES PATENT AND TRADEMARK OFFICE
CERTIFICATE OF CORRECTION

PATENT NO. : 7,077,976 B2  Page 1 of 1
APPLICATION NO. : 11/258301
DATED : July 18, 2006
INVENTOR(S) : Lyle Steimel, James Emerson and Sue Ann Balow It is certified that error appears in the above-identified patent and that said Letters Patent is hereby corrected as shown below:

Title page item 62
After "Related U.S. Application Data", please replace "Division of application No. 11/015781, filed on December 17, 2004, now abandoned.", with --Division of application No. 11/015,781, filed on Dec. 17, 2004, now abandoned; which is a division of application No. 10/238,161, now U.S. patent 6,846,419; which is a continuation-in-part of application No. 10/231,531, filed on Aug. 30, 2002, now abandoned.--

Column 1
Lines 41-42, "temperatures also tends to" should be --temperatures also tend to--

Column 2
Line 13, "phosphate residual, may serve as" should be --phosphate residual may serve as--

Column 3
Line 25, "to affect a corresponding covalent amide bond." should be --to effect a corresponding covalent amide bond.--

Column 5
Lines 29-30, "a phosphonic acids having" should be --a phosphonic acid having--

Column 8
Line 23, Claim 1, "diphosphonic acids and" should be --diphosphonic acid, and--

Signed and Sealed this

Sixteenth Day of January, 2007

JON W. DUDAS
*Director of the United States Patent and Trademark Office*